(12) United States Patent
Armstrong

(10) Patent No.: US 8,086,311 B2
(45) Date of Patent: Dec. 27, 2011

(54) METHOD AND APPARATUS FOR INTEGRATING IMPLANTABLE MEDICAL DEVICE DATA

(75) Inventor: Randolph K. Armstrong, Houston, TX (US)

(73) Assignee: Cyberonics, Inc, Houston, TX (US)

( * ) Notice: Subject to any disclaimer, the term of this patent is extended or adjusted under 35 U.S.C. 154(b) by 844 days.

(21) Appl. No.: 11/656,105

(22) Filed: Jan. 22, 2007

(65) Prior Publication Data

US 2008/0177346 A1 Jul. 24, 2008

(51) Int. Cl.
*A61N 1/362* (2006.01)
(52) U.S. Cl. .......................... 607/31; 607/30
(58) Field of Classification Search ............... 607/2, 30, 607/31, 32, 59, 60, 63; 705/2, 3
See application file for complete search history.

(56) References Cited

U.S. PATENT DOCUMENTS

| | | | |
|---|---|---|---|
| 6,308,099 B1 * | 10/2001 | Fox et al. ..................... | 607/31 |
| 2001/0051787 A1 * | 12/2001 | Haller et al. .................. | 604/66 |
| 2008/0058900 A1 * | 3/2008 | Berthelsdorf et al. ......... | 607/59 |

* cited by examiner

*Primary Examiner* — Carl H Layno
*Assistant Examiner* — Allen Porter, Jr.
(74) *Attorney, Agent, or Firm* — Conley Rose, PC; Jonathan D. Rowell; Darrell N. Fuller

(57) ABSTRACT

Methods and systems for constructing a comprehensive history for an IMD are disclosed. The method includes interrogating an implantable medical device (IMD) with an interrogating external programmer device (EPD), and comparing a unique signature associated with the interrogating EPD to a stored signature, associated with a particular programmer device that most immediately previously programmed the IMD, in memory of the IMD. If the unique signature of the interrogating programmer device is not the same as the stored signature, the method includes recording the stored signature in the interrogating EPD. The method may optionally include replacing the stored signature in the IMD memory with the unique signature of the interrogating EPD if the interrogating EPD programs the IMD. A comprehensive history for the IMD may be constructed by tracing the values in the IMD and the programmer databases.

20 Claims, 6 Drawing Sheets

METHOD AND APPARATUS FOR INTEGRATING IMPLANTABLE MEDICAL DEVICE DATA

BACKGROUND

1. Technical Field

The disclosed subject matter relates generally to implantable medical devices and more particularly to integrating implantable medical device data from various programmer databases for an accurate history of programming for the implantable medical device.

2. Background Information

Various diseases and disorders of the nervous system are associated with abnormal neural discharge patterns. One treatment regimen for such diseases and disorders is drug therapy. Another treatment technique is implantation in the patient of an implantable medical device (IMD) that comprises an electrical signal generator for applying an electrical signal to a target location of the patient's neural tissue. In one such available treatment for epilepsy, an electrical signal is applied to the vagus nerve by a neurostimulator device substantially as described in one or more of U.S. Pat. Nos. 4,702, 254, 4,867,164, and 5,025,807, all of which are incorporated herein by reference.

Some implantable electrical signal generators used for electrical stimulation of neurological tissue operate according to a therapy algorithm programmed into the device by a health care provider such as a physician. The therapy regimen provided to a patient may subsequently be changed by altering one or more therapy parameters defining the electrical signal by reprogramming the neurostimulator after implantation by transcutaneous communication between an external programmer device (EPD) and the implanted neurostimulator. In addition to reprogramming of one or more electrical signal parameters, in some devices the actual software running on the device may be changed to permit significantly or totally different therapy algorithms. The ability to program (and later re-program) the IMD and/or change the software permits a health care provider to customize the therapy provided by the implanted device to the patient's needs, to update the therapy periodically should those needs change, and to update the software of the device, including the operating system, to provide improved therapies on an ongoing basis.

The external programmer device noted above is used to program the IMD to specify different therapeutic algorithms and/or diagnostic routines, and to interrogate the IMD to obtain therapeutic or diagnostic information. A particular patient's IMD may, in the course of treatment, be programmed by a plurality of EPDs. For example, when a physician's office has multiple EPDs, one for each examination room, or when additional physicians consult on a single patient and each physician has his own programmer device, the patient's IMD may be interrogated and/or reprogrammed by any number of EPDs. Each EPD maintains a database locally (i.e., internal to the EDP) of the programming and interrogation information sent to or retrieved from each IMD with which the programmer interacts. Thus, the programming "history" of a single IMD may become distributed across multiple EPDs. The database of a single EPD may be considered comprehensive from the perspective of that particular EPD, however, because an IMD may be programmed or interrogated by multiple EPDs, there is not a single, comprehensive database with respect to a particular patient's IMD. Accordingly, determining the programming history for a particular patient may be difficult, if not impossible.

BRIEF SUMMARY

In accordance with at least one embodiment, a method is disclosed enabling a health care provided to obtain a complete programming history for an IMD for a particular patient. The method comprises interrogating an IMD with a first, interrogating EPD, and comparing a unique signature associated with the first, interrogating EPD device to a stored EPD signature in memory of the IMD. If the unique signature of the first, interrogating EPD is not the same as the stored EPD signature, the method includes retrieving and recording the stored EPD signature from the IMD into a memory of the first, interrogating EPD. The stored signature retrieved from the IMD is associated with the particular EPD that most immediately previously interrogated and/or programmed the IMD. The method may optionally include replacing the stored EPD signature in the memory of the IMD with the unique signature of the first, interrogating EPD, particularly if the interrogating EPD alters settings or programming of the IMD. In order to construct a comprehensive interrogation and/or programming history for the IMD, the method optionally includes retrieving the stored EPD signature from the IMD to determine which EPD most immediately previously programmed the IMD, and comparing the retrieved EPD signature to the first, interrogating EPD's own signature. If the retrieved signature is different from the signature of the first EPD, then the retrieved signature identifies a second EPD, different from the first EPD, as having most immediately interrogated the IMD. The method also includes retrieving the interrogation and/or programming activity and stored signature from the second EPD's database and adding it to a history for the IMD.

In accordance with another embodiment, an IMD comprises an electrical signal generator, a program memory, a data memory, and a programmer history memory. The electrical signal generator includes an instruction processor, and is configured to deliver the electrical signal to a biological tissue. The program memory stores instructions that are directly executable by the instruction processor, and that control, at least in part, the operation of the device. The data memory stores operating parameters that are used by the instruction processor, and that control, at least in part, the operation of the device. The programmer history memory stores a stored EPD signature associated with an EPD that most immediately previously programmed the IMD by communication with the instruction processor. The stored EPD signature stored in the programmer history memory may be retrieved for reconstructing a thread identifying each external device that has interrogated and/or programmed the device.

In accordance with yet another embodiment, an EPD is disclosed that is operable to non-invasively monitor and program an IMD. The EPD includes a unique signature that identifies the EPD, and a local database that stores a record of the EPD activity. The EPD provides a telemetry system operable for non-invasive wireless communication with the IMD. Upon interrogating the IMD, the EPD retrieves a stored signature from the IMD and compares the stored signature to the unique signature of the EPD and, if the stored signature does not match the unique signature, the EPD stores the retrieved signature in the local database.

In accordance with still another embodiment, a medical system is disclosed that comprises an IMD configured to deliver an electrical signal to a biological tissue, and a plurality of EPDs. The IMD includes an instruction processor, a program memory accessible by the instruction processor, and a data memory. The program memory includes stored instructions that are directly executable from the program memory by the instruction processor and which control, at least in part, the operation of the IMD. The data memory stores operating parameters that are used by the instruction processor, and that control, at least in part, the operation of the device. The IMD also includes a programmer history memory that stores a stored EPD signature associated with a particular EPD that most immediately previously programmed the IMD, and an IMD telemetry system operable for non-invasive, wireless communication with one of the plurality of EPDs. Each of the EPDs includes a local database storing a record of the EPD's activity. Upon interrogating the IMD, the interrogating EPD retrieves the stored EPD signature from the programmer history memory to compare the stored EPD signature to a unique signature of the interrogating EPD and, if the stored EPD signature does not match the unique signature of the interrogating EPD, the interrogating EPD stores the retrieved signature in the local database.

The preferred embodiments described herein do not limit the scope of this disclosure.

NOTATION AND NOMENCLATURE

Certain terms are used throughout the following description and claims to refer to particular system components. As one skilled in the art will appreciate, implant companies may refer to a components or groups of components by different names. This document does not intend to distinguish between components or groups thereof that differ in name but not function. In the following discussion and in the claims, the terms "including" and "comprising" are used in an open-ended fashion, and thus should be interpreted to mean "including, but not limited to . . . ."

BRIEF DESCRIPTION OF THE DRAWINGS

For a more detailed description of the preferred embodiments of the present invention, reference will now be made to the accompanying drawings, wherein.

DETAILED DESCRIPTION OF THE PREFERRED EMBODIMENTS

Figure 1:
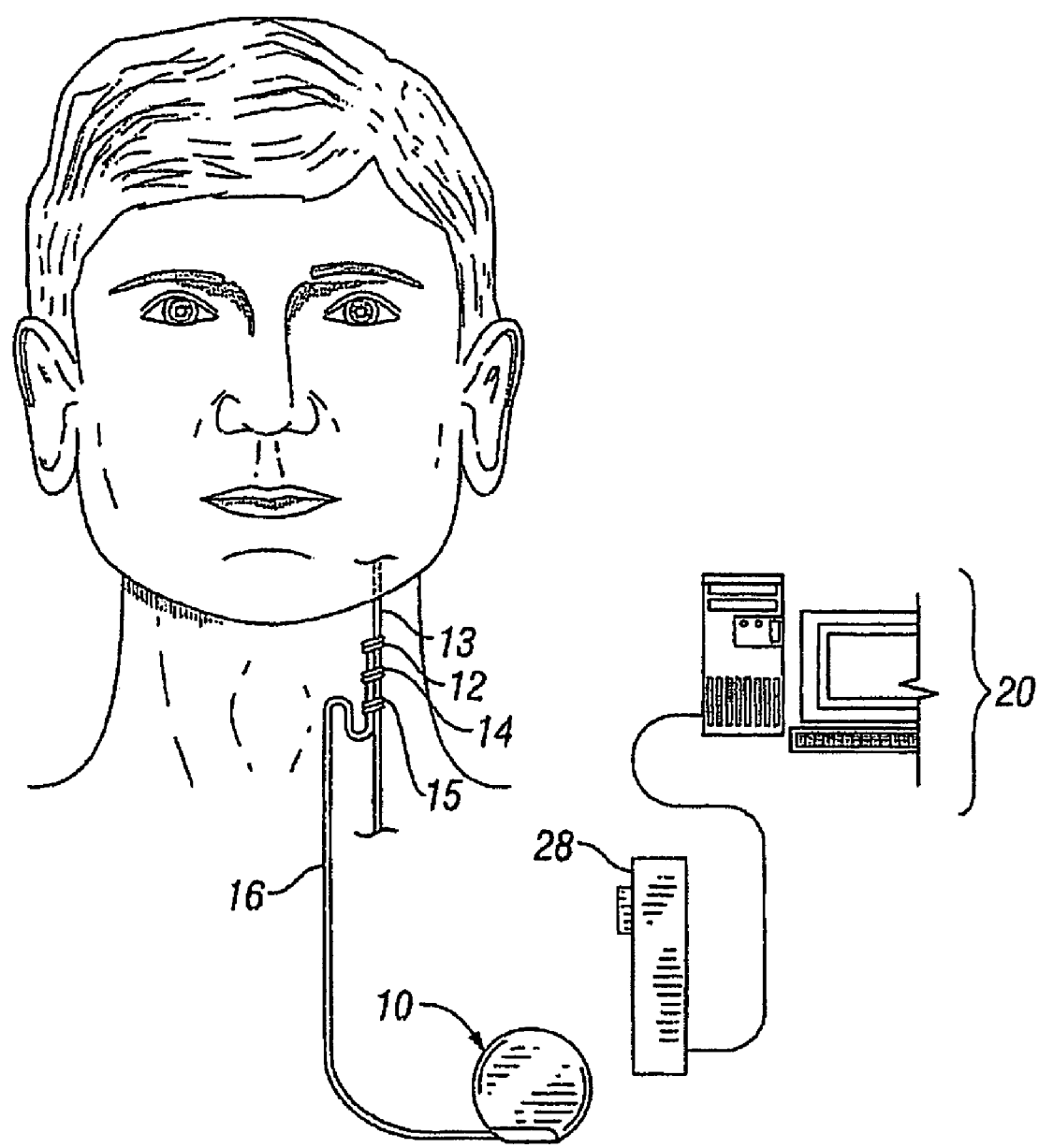
FIG. 1 depicts, in schematic form, an implantable medical device, in accordance with a preferred embodiment of the invention, implanted within a patient and programmable by an external programmer system.

The present invention is susceptible to implementation in various embodiments. The disclosure of specific embodiments, including preferred embodiments, is not intended to limit the scope of the invention as claimed unless expressly specified. In addition, persons skilled in the art will understand that the invention has broad application. Accordingly, the discussion of particular embodiments is meant only to be exemplary, and does not imply that the scope of the disclosure, including the claims, is limited to specifically disclosed embodiments.

The present disclosure includes a method and apparatus to provide integration of separate databases of implantable medical device programming and/or interrogation information. There is a need to identify which local databases (within external programmer devices) are necessary to provide complete data for a particular IMD. For example, if a particular IMD presents to a physician's EPD with program parameters or settings different from those stored in the interrogating EPD's local database for that particular IMD, it is of significant value to know what EPD was last used to change the settings of the IMD and where the data pertaining to that reprogramming (and perhaps other intervening reprogramming sessions that may have occurred since the interrogating EPD last interrogated the particular IMD) may be obtained. Without knowing which programmer was used to change settings, it may not be clear why the settings were changed, or by whom.

The problem is addressed by using available memory in the IMD to store information relating to the most recent EPD to program (or interrogate) the IMD. Upon interrogation (i.e. establishing communication between the interrogating EMD and a particular IMD to retrieve information and/or program the IMD), the EPD reads a memory location in the IMD for a unique EPD signature stored therein. If the EPD signature stored therein matches the unique EPD signature of the interrogating EPD, the EPD proceeds with interrogation and/or programming of the IMD. If the EPD signature stored therein does not match the unique signature of the interrogating EPD, the interrogating EPD copies the EPD signature stored in the IMD memory to its local database, and then overwrites the stored EPD signature with its own unique signature. Thus, if the EPD signature stored in the IMD is different from the signature of a currently interrogating EPD, then a different EPD than the interrogating EPD most immediately previously programmed the IMD, and the currently interrogating EPD records that different EPD's signature for purposes of recording the history for that IMD.

Thus, the IMD stores a unique identifier or EPD signature of the last EPD to program (or interrogate) the IMD, and each EPD that interrogates the IMD retrieves and stores the signature of a different EPD that last programmed or interrogated the IMD. In this way, a complete programming and interrogation history for the IMD may be reconstructed by retrieving data from only the local databases of EPDs that actually programmed (or interrogated) the IMD. In do doing, local databases of EPDs that did not program, or interrogate, the IMD do not need to be checked to see if the particular IMD appears therein. A complete programming and interrogation history thus constructed for the IMD may be useful in troubleshooting devices as well as for providing complete and accurate medical records.

FIG. 1 illustrates an implantable medical device ("IMD") 10 implanted in a patient. The IMD 10 may be representative of any of a variety of medical devices. At least one preferred embodiment of the IMD 10 comprises a neurostimulator for stimulating a neural structure in a patient, particularly a neurostimulator for stimulating a patient's cranial nerve such as a vagus nerve 13. Although the IMD 10 is described below in terms of a vagus nerve stimulation ("VNS") embodiment, the disclosure and claims that follow are not limited to VNS, and may be applied to the stimulation of other tissues such as the trigeminal and/or glossopharyngeal nerves, or to other neural tissue such as one or more brain structures of the patient, spinal nerves, and other spinal structures, as well as non-neural tissue and organs. Although the IMD 10 is described in terms of an electrical signal generator for electrical stimulation of neural tissue, the disclosure is applicable to other types of stimulus generators such as chemical infusion pumps and mechanical stimulation devices for providing stimulation modalities other than, or in addition to, electrical stimulation.

Referring still to FIG. 1, a lead assembly 16 comprising one or more leads is coupled to the IMD 10, in the illustrated embodiment an electrical signal generator. The lead assembly 16 includes one or more electrodes, such as electrodes 12 and 14. Each lead assembly 16 has a proximal end that connects to the IMD 10; the electrodes 12, 14 are coupled to a distal end. At least one electrode 12 or 14, and preferably an electrode pair (12 and 14), is used as a stimulating electrode to deliver electrical signal to target tissues such as the patient's vagus nerve 13. At least one electrode 12, 14 (preferably an electrode pair 12 and 14) may in some embodiments be used as a sensing electrode to detect electrical activity of target tissue (e.g., the vagus nerve 13). In alternative embodiments, separate sensing electrode(s) may be used. The housing (or "can") of the IMD 10 may also be used as a stimulating sensing electrode.

Further still, some embodiments include a combination of stimulation-only electrodes, sensing-only electrodes, and combination stimulation and sensing electrodes. The number of stimulation-capable, sensing-capable, and the total number of electrodes can be selected as desired for the given application. Other additional electrodes can function as sensing electrodes to sense any target parameter in the patient's body, such as, for example, a parameter related to the patient's heart, the patient's blood pH, blood pressure, blood sugar, movement of the patient, or other parameters related to the patient's physical condition. Other types of sensors well known in the art may additionally be used to monitor such parameters. Examples of electrodes suitable for coupling to a vagus nerve 13 to provide VNS therapy to a patient are available from Cyberonics, Inc. (Houston, Tex.) as the Model 300 and Model 301 electrodes. Other suitable electrodes are disclosed in U.S. Pat. No. 4,979,511, incorporated herein by reference in its entirety. An anchoring tether 15 is provided in a lead assembly 16 to provide strain relief, an example of which is also described in U.S. Pat. No. 4,979,511

FIG. 1 also illustrates an external device implemented as an external programmer system 20 for the IMD 10. The external programmer system 20 may comprise a personal computer, personal digital assistant (PDA) device, or other suitable computing device consistent with the description contained herein, as well as a wand 28 used for transmitting and receiving signals to and from the IMD 10. Methods and apparatus for communication between the IMD 10 and an external programmer system 20 are known in the art, including telemetry via an RF communication link. Representative techniques for such communication are disclosed in U.S. Pat. No. 5,304,206, and 5,235,980, both incorporated herein by reference. As explained below, the IMD 10 includes a transceiver (such as a coil) that permits signals to be communicated wirelessly between the wand 28 and the IMD 10. Via the wand 28, the external programmer system 20 generally interrogates and monitors the performance of the IMD 10, and downloads new executable operational programming (i.e., software) and/or therapy parameters into the IMD 10 to alter its operation as desired.

Each external programmer system 20 maintains a local database of external programmer activity, i.e., the programming and interrogation information sent to or retrieved from each IMD 10 with which the programmer interacts. In at least some embodiments, the external programmer device activity may include, for each interaction with an IMD, at least one of: a date of programming the IMD, a time of programming the IMD, an identifier for the IMD programmed, a change made to the programming, and the stored signature stored in the IMD. Additional or difference activities may be applicable as well. The external programmer device activity may include programming information such as the date and time of modification of therapy parameters or programming, and a record of the change in parameters or programming. The external programmer device activity may include interrogation information such as the date and time of interrogation, and the diagnostic information retrieved from the IMD 10 at the time of interrogation, such as performance measurements relating to the IMD 10, and health statistics relating to the patient that are recorded by the IMD 10.

Figure 2:
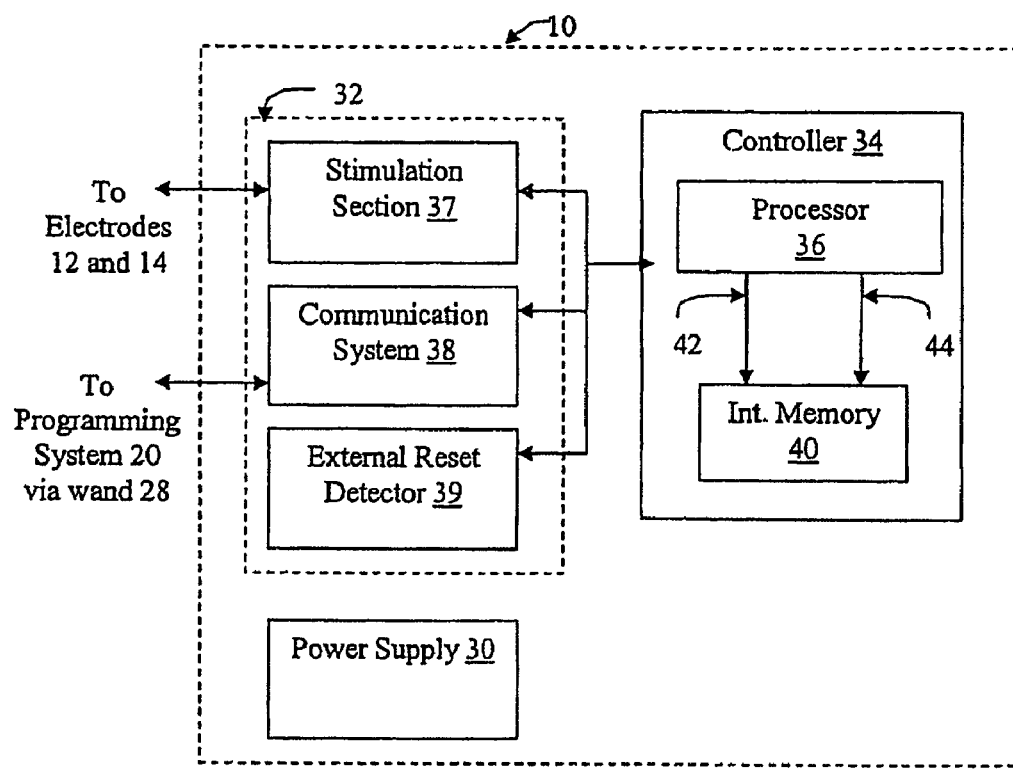
FIG. 2 is a block diagram of the implantable medical device of FIG. 1 and comprising a stimulation and communication unit and a controller.

FIG. 2 shows a block diagram of a preferred embodiment of the IMD 10. As shown, the IMD 10 includes a power supply 30 (e.g., a battery), a stimulation and communication unit ("SCU") 32, and a controller 34. The SCU 32 may comprise, or be referred to as, a "pulse generator" or perform some or all of the functionality of a pulse generator. For example, under the control of controller 34 the stimulation section 37 of the SCU 32 may generate an electrical signal to stimulate a neural structure in a patient. Further, under the control of controller 34 the communication system 38 of the SCU 32 may telemeter data (such as therapy parameters) or operational programming (such as software) to/from the external programmer system 20 via the wand 28. Further, the SCU 32 may comprise an external reset detector 39. In this embodiment, the power supply 30 provides power for both by the SCU 32 and the controller 34. The SCU 32 includes a voltage regulator 58 that receives voltage from the power supply 30 and provides operating voltage for use by the controller 34. In this way, the SCU 32 can control the voltage provided to the controller 34. In an alternative embodiment the SCU 32 may also comprise a sensing unit in communication with one or more body parameter sensors for detecting one or more body parameters of interest.

The controller 34 generally assists, controls, and/or programs the SCU 32. Controller 34 preferably comprises a processor 36 such as a low-power, mixed-signal microcontroller. One suitable processor is available from Texas Instruments, Inc., selected from the MSP430F family of processors. Other suitable processors from the PlC1xF family of processors are available from MicroChip Technology. Other suitable processors may be used and/or integrated into the controller 34, although the processor 36 preferably is capable of processing a variety of sensor inputs, uses low power, and operates at a high speed. In general, however, any suitable processor 36 can be used in the controller 34 to implement the functionality performed by the controller 34 as explained herein. It will be appreciated that some features of the controller 34 may also be provided in whole or in part by the SCU 32, and vice versa. Thus, while certain features of the present invention may be described as comprising part of the SCU 32, it is not intended thereby to preclude embodiments in which the features are provided by the controller. Likewise, certain features described herein as comprising part of the controller 34 are not intended to preclude embodiments in which the features comprise part of the SCU 32.

Figure 3:
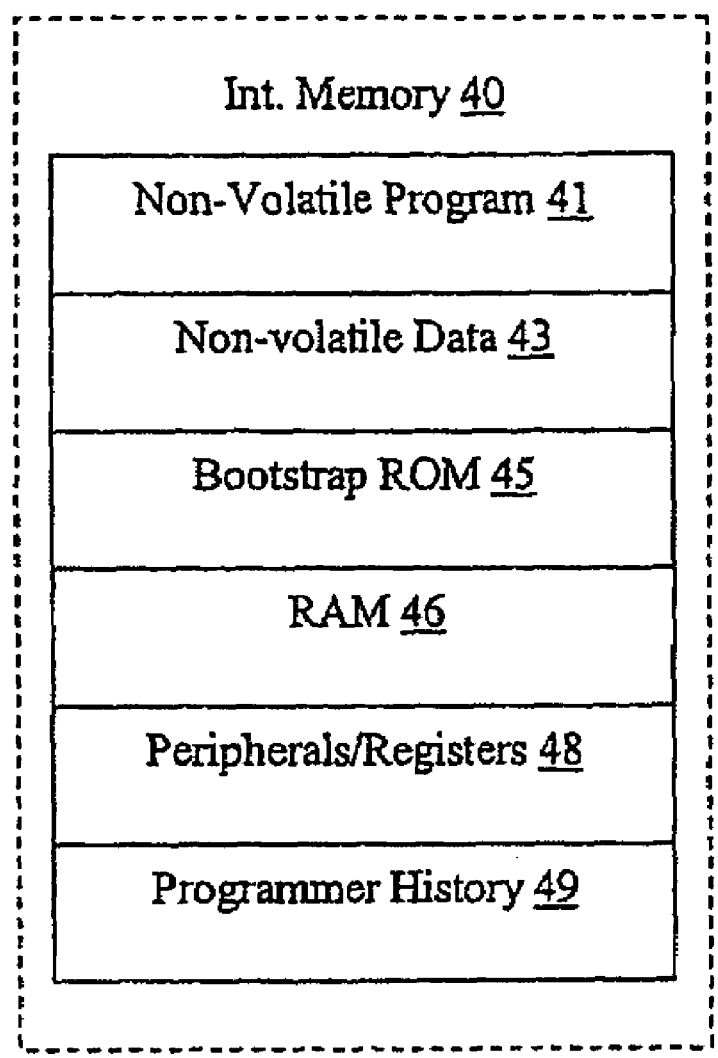
FIG. 3 is a block diagram of the controller memory of the implantable medical device of FIG. 2.

In the embodiment of FIG. 2, the controller 34 additionally comprises a memory 40 integrated into the controller, as explained in greater detail with respect to FIG. 3. The processor 36 of the controller 34 directly executes programs from the integrated memory 40. That is, executable instructions (i.e., operational programming) can be fetched directly from memory 40 for execution by the processor 36 without first copying the instructions to another memory (e.g., a RAM). The integrated memory 40 may be upgraded by erasing one or more segments of the integrated memory 40 and, via the external programmer system 20, writing a new program to the integrated memory 40. Among other functions, in operation, the processor 36 generates an erase control signal 42 and a write control signal 44 that operate on the memory 40.

The processor 36 preferably includes an on-chip memory 40, as shown in greater detail in FIG. 3. The memory 40 preferably comprises a non-volatile, re-programmable memory 41 such as flash memory or EEPROM memory that preferably stores the software to be executed by the processor 36 as well as therapy parameters used by the processor 36 in conjunction with the software. The software to be executed as well as therapy parameters may be stored in combined non-volatile memory or in separate non-volatile memory as shown in FIG. 3, wherein the software to be executed is stored in non-volatile program memory 41 and therapy parameters are stored in non-volatile data memory 43. The voltage required for the controller 34 to re-program its flash memory (via the erase control signal 42 and write control signal 44) may be different than the voltage needed for the controller during other aspects of its operation. The SCU 32 receives voltage from the power supply 30 and provides supply voltage for the controller 34 in its fully operational and standby modes of operation, as well as for programming non-volatile memory contained in the processor 36.

The communication system 38 enables the external wand 28 (FIG. 1) to communicate with the IMD 10. More particularly, in certain embodiments, the communication system 38 permits the external programmer system 20 to program the IMD 10 (i.e., transmit therapy parameters or operational programming to the IMD 10) and to interrogate and monitor its configuration and state (i.e., query and receive signals from the IMD 10). In addition, the communication system 38 also permits the external programmer system 20 (or the patient alone by a suitable manual signaling means such as a magnet) to inform the implantable IMD 10 of the occurrence of a physiological event such as a seizure.

In one embodiment, the SCU 32 and the controller 34 preferably are reset on initial power-on or if the IMD simultaneously detects both a magnetic field and an RF transmission from an external programmer system 20. Whenever a magnetic field is detected by an external reset detector 39, which may comprise, e.g., a Reed switch, in the IMD 10, all current switches (not shown) of the IMD 10 are turned off as a safety precaution. This safety precaution can be temporarily overridden (i.e., the IMD 10 may continue to generate and deliver an electrical signal to stimulating electrode 14). To protect against a "stuck at override" failure, the override preferably resets after a predetermined time interval implemented by the reset detector 39.

Referring to FIG. 3, the integrated memory 40 is shown as comprising memory elements of different types. In one preferred embodiment, the integrated memory 40 is memory that is integrated within the processor 36, though in various other embodiments, the integrated memory 40 may be a separate component that is electrically coupled to the processor 36. In a particular embodiment, shown in FIG. 3, the integrated memory 40 comprises non-volatile program memory 41, non-volatile data memory 43, Bootstrap ROM 45, RAM 46, Peripherals/Registers memory 48, and a Programmer History memory 49, each of which may be an individual memory device, or which may be present together in integrated circuitry.

The Bootstrap ROM 45 may be utilized to load an initial program into the non-volatile program memory 41 during manufacture. After the initial programming is complete, the Bootstrap ROM 45 may no longer be needed or used for loading programming.

Both the non-volatile program memory 41 and the non-volatile data memory 43 may comprise either Flash memory or EEPROM. Additionally, one or more segments of the non-volatile program memory 41 may be erased at a time. In addition to the IMD program that it contains, the non-volatile program memory 41 may, for additional security, contain a known secure program. In one embodiment, the known secure program may be run initially on reset to provide the ability to reload a new program even if the main program has been corrupted or has a significant error in it. The non-volatile data memory 43 may contain therapy parameters that may be programmed or modified at any time by a healthcare provider such as a physician by way of the wand 28 and the programmer system 20. Such programmable therapy parameters defining the electrical signal may include current, pulse width, pulse frequency, on-time and off-time, and duty cycle, according to the nature of the medical treatment and the condition of the patient receiving the treatment.

A variable-size portion of the RAM 46 may be used by the controller 34 as a temporary "stack" to store information during interrupts or function calls. The controller 34 resumes operation after interrupts or functions using the data it had stored on this stack. Additionally, a fixed-size portion of the RAM 46 may be used by the software program to store temporary variables. One example of such data includes values involved in an intermediate calculation. Finally, a fixed-size portion of the RAM 46 may be used by the software program to store dynamic data—that which changes frequently and thus does not need to be stored in a non-volatile manner. One example of such data is an elapsed operation time counter.

The portion of the memory 40 dedicated to peripherals and registers 48 stores the control information.

The programmer history memory 49 may be used by the controller 34 to record a unique EPD signature for the particular EPD that is the most recent external programmer system 20 to alter programming in the IMD. The programmer history memory 49 may optionally also record the unique signature for the EPD that is the most recent external programmer system to interrogate the IMD 10. The unique signature for an external programmer system 20 may comprise, for example, the serial number of the EPD, or any other unique, identifying alphanumeric value assigned to the programmer system. As such, the unique signature can be used to distinguish one EPD from another.

Figure 4:
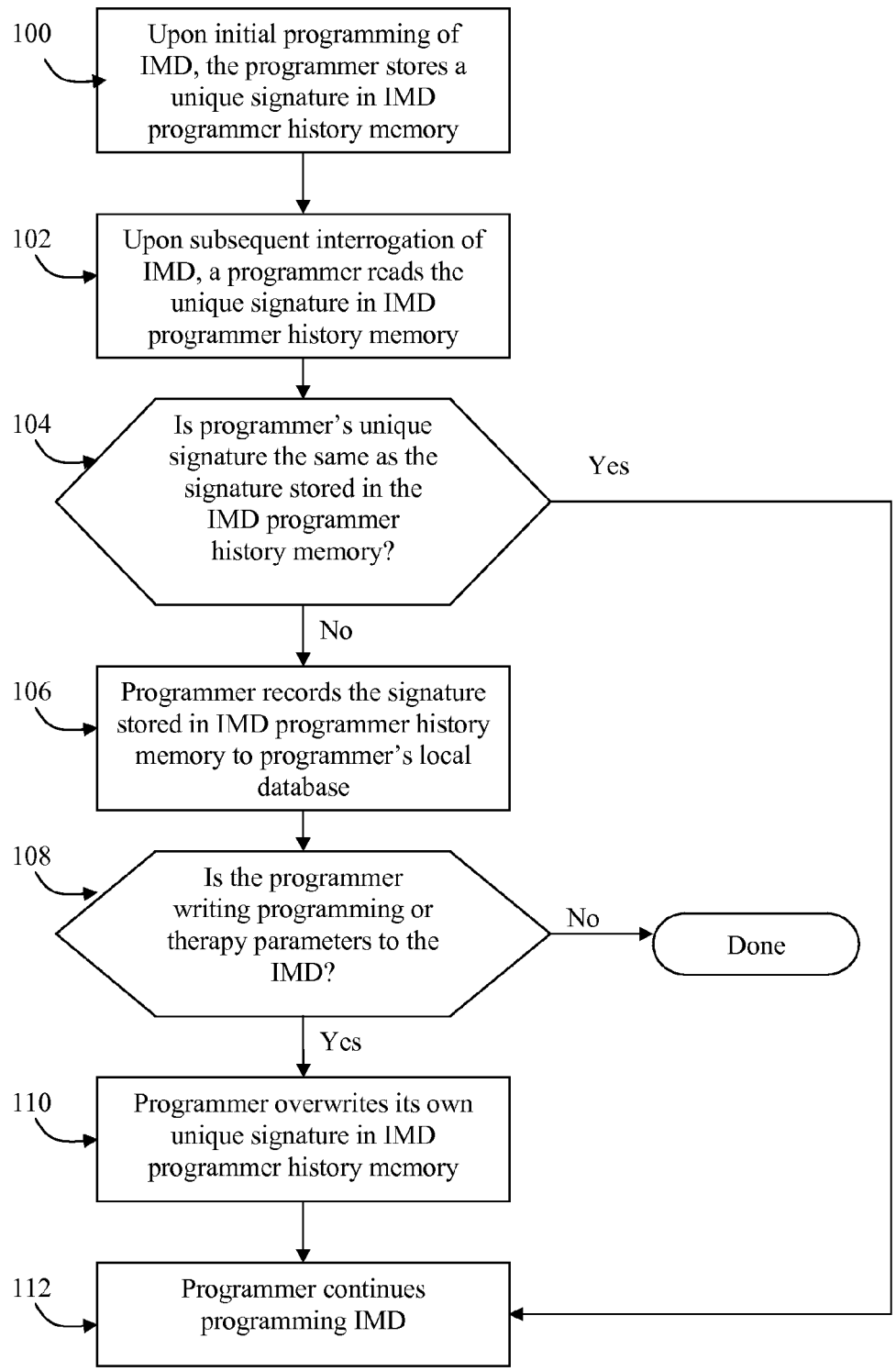
FIG. 4 is a flow chart depicting an exemplary method for integrating implantable medical device data from various external programmer device databases, in accordance with embodiments of the present invention.

Referring to FIG. 4, a flow chart depicting an exemplary method for integrating IMD data from various EPD databases, in accordance with embodiments of the present invention, is shown. The exemplary method begins with initial programming of the IMD 10 by an external programmer system 20. Initial programming of the IMD 10 may occur at the time of manufacture, or following implant in a patient. Upon initial programming of the IMD 10, the programmer 20 stores a unique EPD signature in the programmer history memory 49 (block 100).

Upon subsequent interrogation of the IMD 10 by telemetry, an interrogating EPD reads the unique signature stored in the programmer history memory 49 (block 102). The interrogating EPD used for subsequent interrogation of the IMD 10 may be the same EPD that performed the initial programming, or a different EPD. The interrogating EPD performs a check to determine whether its own unique EPD signature is the same as the signature stored in the programmer history memory 49 of the IMD 10 (block 104).

If the unique signature for the interrogating EPD is the same as the EPD signature stored in the programmer history memory 49 of the IMD 10, then the method continues with interrogation and/or programming the IMD 10 (block 112). If the unique EPD signature for the interrogating EPD is not the same as the EPD signature stored in the programmer history memory 49, the interrogating EPD retrieves the EPD signature stored in the programmer history memory 49 and stores it in its local database (block 106). In this fashion, the interrogating EPD notes the identity of a different EPD that most recently programmed the IMD (i.e., the EPD that programmed the IMD immediately prior to the present EPD interrogation), thereby immediately identifying that a different programmer changed the settings or programming previously.

The method proceeds as the EPD performs a check to determine whether the interrogating EPD is writing new programming or therapy parameters to the IMD, i.e., modifying the therapy or operational programming (block 108). If the interrogating EPD is not writing new programming or therapy parameters to the IMD (i.e., if it is merely retrieving data, not writing data), the method is complete, and there is no need for the EPD to overwrite its own signature in the memory of the IPD. In one optional embodiment, however, the EPD may overwrite its own signature even if it is only interrogating the IMD and not writing data. This would allow a full history of the device to be collected including each EPD that interrogated the device, in addition to EPDs that reprogrammed it. If, on the other hand, the interrogating EPD is writing new programming or therapy parameters to the IMD 10, the EPD overwrites its own unique EPD signature in the programmer history memory 49 (block 110) of the IMD, thereby ensuring that the IMD 10 stores the unique signature of the most recent EPD (now the interrogating EPD) to change the settings or programming.

In other embodiments, the method comprises storing in the programmer history memory 49 the signature of the programmer that most immediately previously programmed the IMD 10 as well as the signature of the programmer that most immediately previously interrogated (without programming) the IMD 10. Thus, the local database of each programmer to interact with a particular IMD 10 will contain identifying information that can be used to reconstruct a thread of every programmer that has interacted with the IMD 10 in any fashion, and to determine the nature (i.e., interrogating or reprogramming) of that interaction.

Figure 5:
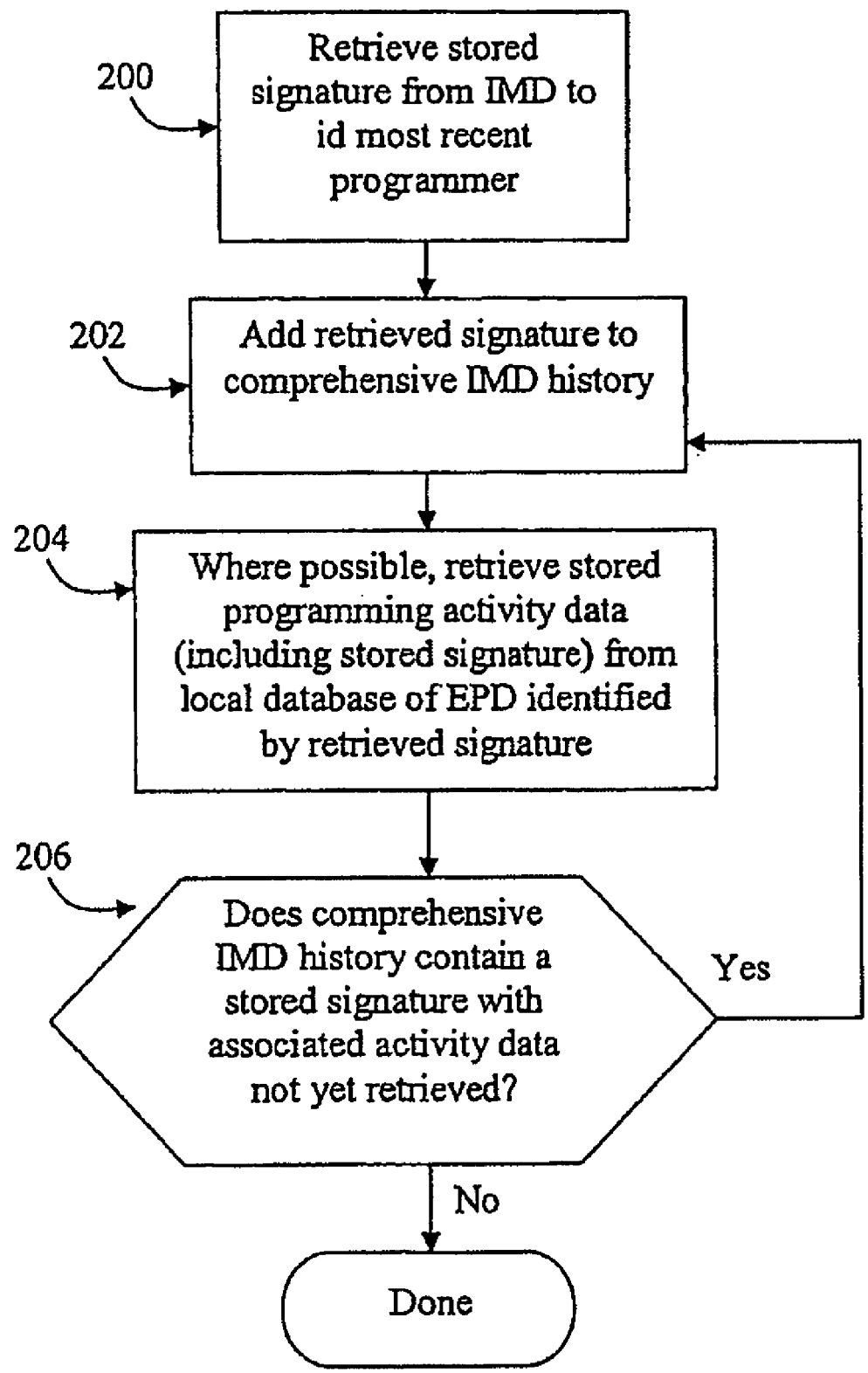
FIG. 5 is a flowchart depicting an exemplary method for reconstructing a comprehensive programming history for an implantable medical device, in accordance with embodiments of the present invention.

Referring to FIG. 5, a flow chart is shown depicting an exemplary method for reconstructing a comprehensive history of IMD data from various EPD databases, in accordance with embodiments of the present invention. The exemplary method begins with the EPD retrieving the stored signature from the memory of the IMD in order to identify the EPD that most recently (i.e., prior to the interrogation by the interrogating EPD) programmed or interrogated the IMD (block 200). In step 202, the retrieved signature is added to a comprehensive history record for the IMD, and preferably a date and time at which the retrieved EPD signature was obtained is also stored with the signature. The method proceeds with retrieving from the local database of an EPD identified by the retrieved signature (i.e., an EPD different from the interrogating EPD that previously programmed the IMD) data associated with the programming and/or interrogation in which the EPD stored its signature in the IMD (block 204). Specifically, the method includes obtaining data such as the date and time of the reprogramming, and the programming parameters as they existed prior to the EPD changing them, as well as the specific changes made by the EPD during the reprogramming exercise. Additional details that may have been captured or obtained during the office visit at which the reprogramming or interrogation occurred may also be retrieved. This data may include patient data such as medications taken by the patient for a period prior to the reprogramming office visit, quality-of-life information, and other information associated with a time period no longer available to the interrogating EPD but which are still stored in memory of the EPD that most recently interrogated/programmed the IMD. Step 204 may include retrieving data from more than one EPD. In such instances, the data is preferably retrieved from the multiple EPDs in the reverse order in which the EPDs programmed the device, i.e., data is preferably obtained in the order of the most recent EPD programming the IMD, to the next most recent, and continuing, where necessary, to the first EPD that programmed the IMD. Use of a date and/or timestamp in conjunction with the storage of an EPD signature allows the data to be obtained, stored and analyzed in the proper sequence.

In block 206, the comprehensive IMD history is analyzed to determine whether the IMD history contains a stored signature for which the data associated with the programming/interrogation by that EPD has not yet been retrieved from its local database. If the IMD history does contain a stored signature for which the data has not yet been retrieved, the method returns to block 202 to obtain the data. If there is no stored signature for which the data associated with the reprogramming/interrogation has not been obtained, the method, and the reconstruction of the comprehensive IMD history, is complete. The comprehensive IMD history may be reconstructed, for example, in a hardcopy printout, in an electronic compilation in a comprehensive "head" programmer, or in an electronic compilation in a central data collection system, such as a computer with which each programmer is synchronized.

Figure 6:
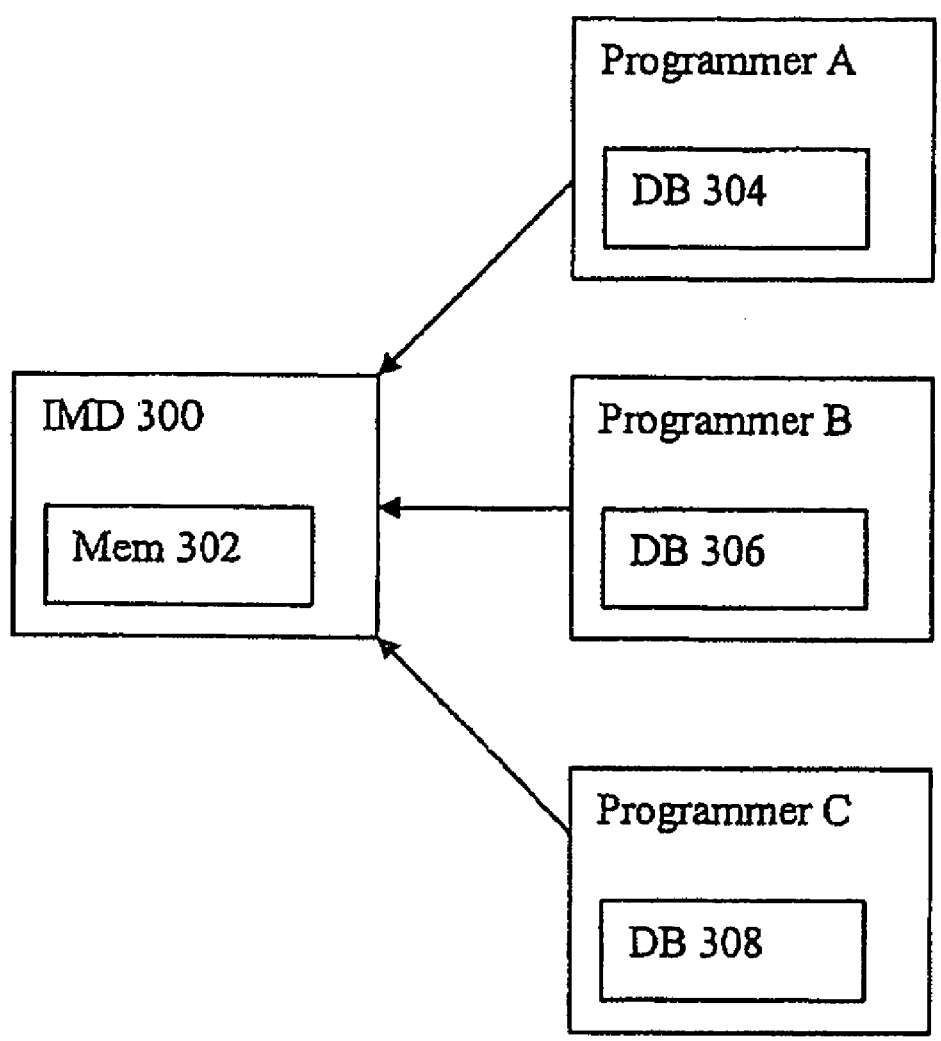
FIG. 6 is a block diagram illustrating an example of the methods of FIGS. 4 and 5 in accordance with embodiments of the present invention.

An illustrative example clarifies the methods of FIGS. 4 and 5. Referring to FIG. 6, a block diagram is provided of a medical system for reconstructing a comprehensive data history of an IMD from various EPD databases. IMD 300 having programmer history memory 302 is shown, and may be programmed by a plurality of EPDs A, B, and C. While three EPDs are shown in FIG. 6, any number of EPDs may be employed in the course of treating a patient having programming a given IMD. The EPDs each include a local database of programmer device activity, shown as DB 304, DB 306, and DB 308 respectively.

In accordance with the method of FIG. 4, EPD A performs the initial programming of the IMD 300, and stores its own unique signature of EPD A in the IMD's programmer history memory 302 as well as in its own database 304. Subsequently, EPD B performs a programming of the IMD 300 to alter the settings. EPD B reads the signature of EPD A from the programmer history memory 302 of the IMD 300 and determines that the retrieved signature of EPD A is not the same as its own unique signature, and thus, EPD B records the signature of EPD A to its local database 306, and then overwrites its own signature, i.e., the signature for EPD B, in the IMD's programmer history memory 302. After the programming session is complete, EPD B also preferably records the signature of EPD A to a comprehensive IMD history.

Subsequently, EPD C establishes communication with the IMD 300 to update the programming. EPD C reads the signature of EPD B from the programmer history memory 302 of IMD 300 and determines that the retrieved signature of EPD B is not the same as its own signature, and thus, EPD C records the signature of EPD B to its local database 398, and then overwrites its own signature, i.e., the signature for EPD C, in the IMD's programmer history memory 302.

Thus, having been sequentially programmed by EPD A, EPD B, and EPD C, in that order, the IMD programmer history memory stores the signature for EPD C as the most recent programmer to program the IMD. EPD C stores the signature of EPD B as the programmer prior to EPD C to program the IMD, and preferably updates a comprehensive IMD history to reflect the fact that EPD B programmed the IMD 300 at a particular date and time. EPD B stores the signature of EPD A as the programmer prior to EPD B to program the IMD, and preferably updates the comprehensive IMD history to reflect the fact that EPD A programmed the IMD 300 at a particular date and time. EPD A stores its own signature, indicating that EPD A performed the initial programming of the IMD.

While each programmer stores a comprehensive history of its own interactions with any number of IMDs, it is desirable to have a centralized comprehensive history of a particular IMD 300 without having to poll every single EPD that could possibly have interacted with the IMD, regardless of whether the programmer actually did interact with the IMD. Such a method would not only be time consuming under the best of circumstances, but may not even be possible where particular EPD is lost, damaged, or replaced. Illustrating the method of FIG. 5, a comprehensive IMD history for IMD 300 may be maintained, either by automatic electronic performance of one embodiment of the method disclosed herein, or by manual performance thereof. IMD 300 may also be interrogated by a computer maintaining the comprehensive history for the IMD to retrieve from the programmer history memory 302 the EPD signature for the EPD that most recently programmed the IMD 300. Thus, in the example, the signature for EPD C would be retrieved from the programmer history memory 302 of IMD 300.

Having retrieved the EPD signature identifying EPD C, in the example, proceeding to EPD C, the signature stored in EPD C's database 308 may be retrieved, i.e., the signature for EPD B. According to one embodiment of the method, the data associated with the programming activity for EPD C is also retrieved at the same time as the signature for EPD B. The programming activity data for EPD C and the signature for EPD B are added to the comprehensive history for the IMD. Noting that the signature for EBD B is in the history, the computer will preferably check to determine whether or not the data associated with the programming activity for EPD B has been retrieved, and the method proceeds with EPD B.

Proceeding to EPD B (identified as having programmed the IMD prior to EPD C), the signature stored in the local database 306 of EPD B is retrieved along with, if not already obtained, the data associated with the programming activity of EPD B. In this example, the signature for EPD A is retrieved from database 306. The retrieved signature for EPD A and the programmer activity data for EPD B are added to the comprehensive history for the IMD. The computer will then preferably check to determine if the data associated with the programming performed by EPD A is already in the comprehensive history, and if not, the method proceeds with EPD A.

EPD A (identified as programming the IMD prior to Programmer B), may be interrogated by the computer to retrieve the signature stored in the local database 304 of EPD A which is, in this example, the signature for EPD A itself. The data associated with the programming performed by EPD A may then be obtained and added to the comprehensive history for the IMD 300. Noting that the activity has been retrieved from each programmer whose signature has been added to the comprehensive IMD history, the method is complete.

Methods of the invention may be performed in various manners (i.e. automatically electronically or manually), and may be performed over again at any time that an up-to-date comprehensive history for an IMD is required.

While preferred embodiments of the present invention have been shown and described, modifications thereof can be made by persons skilled in the art without departing from the spirit and teachings of the invention. The embodiments described herein are exemplary only, and are not intended to limit the scope of protection provided herein.

What is claimed is:

1. A method for obtaining a programming history for an implantable medical device (IMD) for a patient, comprising:
   interrogating the IMD with an interrogating external programmer device (EPD);
   retrieving a stored signature from memory of the IMD;
   comparing a unique signature associated with the interrogating EPD to the retrieved signature from the IMD;
   when the retrieved signature from the IMD is different than the unique signature associated with the EPD, replacing the stored signature in the memory of the IMD with the unique signature of the interrogating EPD and storing the retrieved signature from the IMD into the EPD;
   wherein the retrieved signature is associated with a particular EPD that most immediately previously established communications with the IMD, said retrieved signature is part of the programming history for the IMD;
   communicating the retrieved signature from the interrogating EPD to a display device; and
   displaying, with the display device, the retrieved signature to a user.

2. The method according to claim 1, further comprising storing the retrieved signature in a memory of the interrogating EPD.

3. The method according to claim 2, wherein storing the retrieved signature in a memory of the EPD further comprises writing the retrieved signature to a local database of the interrogating EPD.

4. The method according to claim 1, wherein the stored signature is stored in a programmer history memory module of the IMD.

5. The method according to claim 1, wherein the unique signature comprises a serial number of the programmer device.

6. The method according to claim 1, further comprising reconstructing a comprehensive history for the IMD including the signature for each EPD that has programmed the IMD.

7. The method according to claim 6, wherein reconstructing the comprehensive history comprises retrieving the stored signature from the IMD to determine which EPD most immediately previously programmed the IMD.

8. The method according to claim 6, wherein reconstructing the comprehensive history comprises retrieving a second signature from the EPD.

9. The method according to claim 1, further comprising:
   retrieving from the IMD a timestamp associated with a retrieved stored signature, said timestamp indicating when the EPD identified by the retrieved stored signature programmed said IMD.

10. The method according to claim 1, further comprising generating an indicator when the interrogating EPD detects previous programming by a programmer having a different signature.

11. The method according to claim 1, wherein the unique signature comprises an alphanumeric value assigned to the programmer device.

12. The method according to claim 1 further comprising reconstructing a comprehensive history for the IMD, wherein reconstructing the comprehensive history comprises:
- retrieving the stored signature from the IMD to determine which EPD most immediately previously programmed the IMD;
- retrieving a second signature from the EPD identified by the stored signature; and storing the both signatures to a comprehensive IMD history in a computer.

13. A method, comprising:
- interrogating an implantable medical device (IMD) with an interrogating external programmer device (EPD);
- comparing a unique signature associated with the interrogating EPD to a stored signature in memory of the IMD;
- when the stored signature from the memory of the IMD is different than the unique signature associated with the interrogating EPD, retrieving the stored signature from the memory of the IMD; and
- reconstructing a comprehensive history for the IMD including the signature for each EPD that has programmed the IMD;
- wherein reconstructing the comprehensive history comprises retrieving the stored signature from the IMD to determine which EPD most immediately previously programmed the IMD, retrieving a second signature stored in a local database of the EPD identified by the stored signature and storing the stored signature and the second signature to a comprehensive IMD; and
- wherein the retrieved signature is associated with a particular EPD that most immediately previously established communications with the IMD;
- communicating the comprehensive IMD history to a display device; and
- displaying, with the display device, the comprehensive IMD history to a user.

14. The method according to claim 13, further comprising:
- retrieving data associated with programming activity performed by at least one of the interrogating EPD and the EPD identified by the second signature; and
- storing the retrieved data associated with programming activity in the comprehensive IMD history.

15. The method according to claim 13, further comprising:
- if the comprehensive IMD history contains a signature for which data associated with programming activity has not yet been retrieved, retrieving the data associated with programming activity from the EPD programmer identified by that signature, and adding the retrieved data to the comprehensive IMD history.

16. The method according to claim 13, further comprising replacing the stored signature in the memory of the IMD with the unique signature of the current interrogating EPD.

17. The method according to claim 13, further comprising storing the retrieved signature in a memory of the interrogating EPD.

18. The method according to claim 17, wherein storing the retrieved signature in a memory of the EPD further comprises writing the retrieved signature to a local database of the interrogating EPD.

19. The method according to claim 13, wherein the stored signature is stored in a programmer history memory module of the IMD.

20. The method according to claim 13, wherein the unique signature comprises a serial number of the programmer device.

* * * * *